(12) United States Patent
Chance (10) Patent No.: US 6,397,099 B1
(45) Date of Patent: May 28, 2002

(54) NON-INVASIVE IMAGING OF BIOLOGICAL TISSUE (75) Inventor: Britton Chance, Marathon, FL (US)

(73) Assignee: Non-Invasive Technology, Inc., Philadelphia, PA (US)

( * ) Notice: Subject to any disclaimer, the term of this patent is extended or adjusted under 35 U.S.C. 154(b) by 0 days.

(21) Appl. No.: 09/266,982

(22) Filed: Mar. 12, 1999

Related U.S. Application Data (63) Continuation of application No. PCT/US97/16309, filed on Sep. 15, 1997, which is a continuation-in-part of application No. 08/713,401, filed on Sep. 13, 1996, now Pat. No. 5,853,370, which is a continuation-in-part of application No. 08/466,392, filed on Jun. 6, 1995, now Pat. No. 5,954,053, which is a division of application No. 08/150,084, filed on Nov. 15, 1993, now Pat. No. 5,873,821, which is a continuation of application No. PCT/US92/04153, filed on May 18, 1992.

(51) Int. Cl.$^7$ .................................................. A61B 5/00

(52) U.S. Cl. .................... 600/473; 600/323; 600/328; 600/431; 600/476

(58) Field of Search .................... 600/310, 322–324, 600/326, 328, 329, 340, 431, 473, 476, 479

(56) References Cited

U.S. PATENT DOCUMENTS

| 3,638,640 A | 2/1972 | Shaw |
| 4,281,645 A | 8/1981 | Jobsis |
| 4,515,165 A | 5/1985 | Carroll |
| 4,937,526 A | 6/1990 | Ehman et al. |
| 4,940,453 A | 7/1990 | Cadwell |
| 5,088,493 A | 2/1992 | Giannini et al. |
| 5,090,415 A | 2/1992 | Yamashita et al. |

(List continued on next page.)

FOREIGN PATENT DOCUMENTS

| DE | 43 03 047 A | 8/1994 |
| WO | WO 88/01485 | 3/1988 |
| WO | WO 92/20273 | 11/1992 |
| WO | WO 93/25145 | 12/1993 |
| WO | WO 95/02987 | 2/1995 |
| WO | WO 96/20638 | 7/1996 |

OTHER PUBLICATIONS

Apicella et al., "Fast multi–modality image matching", SPIE, vol. 1092, pp. 252–263, 1989.

Arridge, "The Forward and Inverse Problems in Time Resolved Infra–Red Imaging", Medical Optical Tomography: Functional Imaging and Monitoring, SPIE Optical Engineering Press, vol. IS11, pp. 35–64, 1993.

(List continued on next page.)

Primary Examiner—Ruth S. Smith
(74) Attorney, Agent, or Firm—Fish & Richardson P.C.

(57) ABSTRACT

An optical system for in vivo, non-invasive imaging of tissue change includes an optical module with an array of input ports and detection ports located in a selected geometrical pattern to provide a multiplicity of arrayed single source, single detector pairs engaged directly with the subject; a spectrophotometer including a light source constructed to introduce electromagnetic radiation of visible or infra-red wavelength into the examined tissue successively at the input ports, the wavelength being sensitive to a constituent of the imaged tissue; a detector constructed to detect, at the detection ports, radiation of the selected wavelength that has migrated in the tissue from respective input ports; and a processor receiving signals of the detected radiation from the detector, and constructed and arranged to create a defined spatial image of the tissue by effectively producing from signals from the multiplicity of arrayed single source, single detector pairs, a succession of data sets representing, from a selected view, a succession of spatial images of the tissue, and an image data set related to differences between data of the successive data sets. Imaging instruments and a method are also described.

21 Claims, 6 Drawing Sheets

U.S. PATENT DOCUMENTS

| | | |
|---|---|---|
| 5,143,081 A | 9/1992 | Young et al. |
| 5,158,090 A | 10/1992 | Waldman et al. |
| 5,198,977 A | 3/1993 | Salb ........................ 364/413.01 |
| 5,218,962 A | 6/1993 | Mannheimer et al. |
| 5,287,276 A | 2/1994 | Crawford et al. |
| 5,402,778 A | 4/1995 | Chance |
| 5,431,170 A | 7/1995 | Mathews |
| 5,853,370 A | * 12/1998 | Chance ........................ 600/473 |

OTHER PUBLICATIONS

Benaron et al., "A Medical Prespective at the Threshold of Clinical Optical Tomography", Medical Optical Tomography: Functional Imaging and Monitoring, SPIE Optical Engineering Press, vol. IS11, pp. 3–9, 1993.

Colak et al., "Optical Back Projection Tomography in Heterogeneous Diffusive Media", Advances in Optical Imaging and Photon Migration, TOPS (Trends in Optics & Photonics Series), vol. 2, pp. 282–289, Mar. 1996.

Feng et al., "Analytical perturbation theory of photon migration in the presence of a single absorbing or scattering defect sphere", SPIE, vol. 2389, pp. 54–63, 1995.

Hajnal et al., "Artifacts Due to Stimulus Correlated Motion in Functional Imaging of the Brain", MRM, pp. 283–291, 1994.

Hoshi et al., "Detection of dynamic changes in cerebral oxygenation coupled to neuronal function during mental work in man", Neuroscience Letters, vol. 150, pp. 5–8, 1993.

Maki et al., "Spatial and temporal analysis of human motor activity using noninvasive NIR topography", Med. Phys., vol. 22, No. 12, pp. 1997–2005, 1995.

Matcher et al., "Absolute quantification methods in tissue near infrared spectroscopy", SPIE, vol. 2389, pp. 486–495, 1995.

Nioka et al., "Optical Imaging of Breast Tumors with Various Methods", Oxygen Transport to Tissue, vol. XVIII, pp. 227–232, 1997.

Oda et al., "Non–Invasive Hemoglobin Oxygenation Monitor and Computerized Tomography of NIR Spectrophotometry", SPIE, vol. 1431, p. 204, 1991.

Ogawa et al., "The Sensitivity of Magnetic Resonance Image Signals of a Rat Brain to Changes in the Cerebral Venous Blood Oxygenation", Magnetic Resonance in Medicine, vol. 29, pp. 205–210, 1993.

Pelizzari et al., "Accurate Three–Dimensional Registration of CT, PET and/or MR Images of the Brain", J. Computer Assisted Tomography, vol. 13, No. 1, pp. 20–26, 1989.

Polishchuk et al, "Non–Euclidean diffusion and 'Fermat' photons in turbid media", SPIE, vol. 2389, pp. 6–9, 1995.

Sevick et al., "The physical basis of biomedical optical imaging using time–dependent measurements of photon migration in the frequency–domain", Medical Optional Tomography: Functional Imaging and Monitoring, SPIE, Optical Engineering Press, vol. IS11, pp. 485–512, 1993.

Sevick et al., "Quantitation of Time–and Frequency–Resolved Optical Spectra for the Determination of Tissue Oxygenation", Analytical Biochem., 195:330–351, 1991.

Singer et al., "Image Reconstruction of the Interior of Bodies that Diffuse Radiation", Science, vol. 228, pp. 990–993, 1990.

Woods et al., "Rapid Automated Algorithm for Aligning and Reslicing PET Images", J. Computer Assisted Tomography, vol. 16, No. 4, pp. 620–633, 1992.

* cited by examiner

| | |
|---|---|
| A | -0.200 |
| B | |
| C | -0.150 |
| D | |
| E | -0.100 |
| F | |
| G | -0.050 |
| H | |
| I | 0.000 |
| J | |
| K | 0.050 |
| L | |
| M | 0.10 |
| N | |
| O | 0.150 |
| P | |

NON-INVASIVE IMAGING OF BIOLOGICAL TISSUE

PRIORITY CLAIM

This application is a continuation of PCT Application PCT/US97/16309, filed on Sep. 15, 1997, which is a continuation of U.S. application Ser. No. 08/713,401, filed on Sep. 13, 1996, now U.S. Pat. No. 5,853,370. This application is also a continuation-in-part of U.S. application Ser. No. 08/466,392, filed on Jun. 6, 1995, now U.S. Pat. No. 5,954,053, which is a divisonal of U.S. application Ser. No. 08/150,084, Nov. 15, 1993 now U. S. Pat. No. 5,873,821, which is a continuation of PCT Application PCT/US92/04153, filed on May 18, 1992.

The invention provides proof in principle of the practicality for medical purposes of imaging body tissue, and in particular, neural tissue, especially the brain, using spectrophotometric techniques.

Certain prior work has produced low resolution shadowgrams of the exterior of the cortex, lacking edges or defined contours.

We have shown that by employing an array of ports for a set of single source, single detector pairs, and by implementing the system to acquire a sequence of data sets, distinct difference image data sets can be realized that are useful in diagnosis and treatment, e.g. on a real time basis, with relatively low expense. Blood volume and oxygenation, for instance, can be directly imaged.

We have demonstrated in brain models and human brains, that an optical imaging device can localize the activated area of the human brain. We have produced defined images that show that single functions of the brain such as observing an object (visual), moving a small part of the body (sensory motor) and thinking (cognition) appear to activate only an area as small as 0.5 to 1 cm of the brain cortex. The place of activation observed from the produced image was where it was expected. In the case of side-by-side source and detector pair, between which the probability pattern of photons takes a banana shape, the theoretical resolution and sensitive depth depends on the source-detector distance (half of the distance). By selection of the source-detector distance, a resolution of the image as good as 1.25 cm has been obtained. Imaging of white brain matter to selected depths is realized by increasing the spacing up to 7 cm.

By acquiring the images quickly (2 to 8 seconds for a data set, within about 20 seconds for a distinct difference image data set) we have demonstrated the practicability of optical imaging as a tool for the fields of psychiatry, psychology, neurology, patho-physiology, surgery, etc. Direct contact of the input and output ports with the subject lead to favorable signal-to-noise ratio that leads to good image resolution. In particular, direct contact of an array of miniature sources (lamps or diodes) and detectors has provided ample signal.

By the ability to obtain images in a short span of time (within a few minutes, typically within less than a minute), the field of real-time noninvasive and nonharmful optical monitoring of tissue at a depth from the surface is shown to be within practical grasp.

Using optical techniques avoids tissue damage, can be done inexpensively, and can provide other advantages compared to MRI, FMRI, P.E.T., E.G.G. mapping and the like.

For instance, the source and detector module are readily affixed to the head or other body part, as by a helmet, and alleviate a serious problem of artifacts related to movement of the subject relative to the detector during the time of taking an image that occurs with other imaging techniques.

The work reported here leads to diagnosis of impairment due to trauma, stroke, Alzheimer's disease, and various patho-physiological manifestations. Furthermore the invention, together with current knowledge in the field, shows practicality of the technique in wide fields of utility, encompassing the detection and imaging of local perturbation or change related broadly to mental function, physiological function and biochemical function.

It is shown that light sources that provide no safety hazard, at relatively low cost can be usefully employed in true imaging. By employing difference measurements, the uncertainties normally limiting continuous wave spectroscopy (CWS) to trend indications are avoided. The greater information content of phase modulation and time resolved spectroscopy leads to even more informative images.

According to one important aspect of the invention, an optical system is provided for in vivo, non-invasive imaging of tissue change comprising an optical module including an array of input ports and detection ports located in a selected geometrical pattern to provide a multiplicity of arrayed single source, single detector pairs engaged directly with the subject, a spectrophotometer including a light source means constructed to introduce electromagnetic radiation of visible or infra-red wavelength into the examined tissue successively at the input ports, the wavelength being sensitive to a constituent of the imaged tissue, detector means constructed to detect, at the detection ports, radiation of the selected wavelength that has migrated in the tissue from respective input ports, and a processor receiving signals of the detected radiation from the detector means, and constructed and arranged to create a defined spatial image of the tissue by effectively producing from signals from the multiplicity of arrayed single source, single detector pairs, a succession of data sets representing, from a selected view, a succession of spatial images of the tissue, and an image data set related to differences between data of the successive data sets.

In another important aspect of the invention, an optical system is provided for in vivo, non-invasive functional neuroimaging of tissue comprising a stimulator constructed to stimulate a selected functional activity of neural tissue of interest, an optical module including an array of input ports and detection ports located in a selected geometrical pattern to provide a multiplicity of arrayed single source, single detector pairs engaged directly with the subject, a spectrophotometer including light source means constructed to introduce electromagnetic radiation of visible or infra-red wavelength into the examined neural tissue successively at the input ports, the wavelength being sensitive to a tissue constituent associated with a physiological response of the imaged functional activity, detector means constructed to detect, at the detection ports, radiation of the selected wavelength that has migrated in the stimulated neural tissue from respective input ports, and a processor receiving signals of the detected radiation from the detector means, and constructed and arranged to create a defined spatial image of the functional activity of neural tissue by effectively producing from the signals from the multiplicity of arrayed single source, single detector pairs, a first data set representing, from a selected view, a spatial image of the neural tissue at rest, a second data set representing, from the same selected view, a spatial image of the neural tissue during stimulation, and a functional image data set that is related to the differences between the first and second data sets, over the sets.

Preferred embodiments of these aspects of the inventions have one or more of the following features.

The optical module is constructed to maintain a selected distance between the input and detection ports for the respective source-detector pairs during the production of the first and second data sets, the distance being selected according to the tissue depth desired to be imaged.

The optical module or an associated set of the modules is constructed to take readings at different depths to produce 3D data sets from which an image date set may be produced.

The processor is adapted to produce the image data set by implementing an optical tomography algorithm.

The optical tomography algorithm preferably employs factors related to determined probability distribution of photons attributable to the scattering character of the tissue being imaged.

The optical system is constructed to form the image data set from a part of the head. In particular embodiments the optical system is constructed to form the functional image data set from below the surface region of the cortex.

The stimulator is constructed to stimulate the visual cortex, the cognitive cortex, the sensory motor cortex, or spinal tissue.

In various embodiments the stimulator is constructed to deliver electrical signals to selected tissue, apply an electrical field to selected tissue, or deliver magnetic signals to selected tissue.

In various embodiments the image set is related to at least one of the group consisting of blood volume, hemoglobin oxygenation or deoxygenation, photon absorption coefficient, photon scattering coefficient, refractive index, change in magnetic field, change in electric field, production of or change of a specific tissue constituent, and production of or change in the concentration of a pigment.

In various embodiments the tissue constituent is an endogenous pigment, for example hemoglobin, or an exogenous pigment, for example a selected contrast agent.

The source means, the detector means, the source to detector distance, and the rate of excitation and detection are selected to enable an image data set to be obtained within a short time, i.e., within minutes, preferably within a minute or less.

In certain embodiments, the spectrophotometer further includes a first oscillator constructed to generate a first carrier waveform at a first frequency on the order of $10^8$ Hz, the first frequency having a time characteristic compatible with the time delay of photon migration from an input port to a detection port in the examined tissue, the light sources means being coupled to the first oscillator and constructed to generate the radiation modulated by the first carrier waveform, a phase detector constructed to determine change in waveform of the detected radiation relative to the waveform of the introduced radiation and measure therefrom the phase shift of the detected radiation at the wavelength, the phase-shifted radiation being indicative of scattering or absorptive properties of the examined tissue, and the processor constructed to create the functional image data set based at least in part on the measured phase shift.

Preferably, this optical system further comprises a second oscillator constructed to generate a second waveform at a second frequency, the detector means arranged to receive a reference waveform at a reference frequency offset by a frequency on the order of $10^3$ Hz from the first frequency and to produce a signal, at the offset frequency, corresponding to the detected radiation, and the phase detector adapted to compare, at the offset frequency, the detected radiation with the introduced radiation and to determine therefrom the phase shift at the wavelength.

In certain other embodiments the spectrophotometer includes a light source means that is constructed to generate pulses of radiation of the wavelength, the pulses having duration on the order of a nanosecond or less, the detector means being constructed to detect over time photons of modified pulses that have migrated in the tissue from the input ports, an analyzer, connected to the detector means, adapted to determine a change in the pulse waveform shape of the detected pulses relative to the introduced pulses, at the wavelength, and the processor being constructed and arranged to create the image data set based on the determined pulse waveform change.

Preferably, this processor is constructed and arranged to calculate the effective pathlength of photons of the wavelength migrating between the input and detection ports in conjunction with creating the image data set.

In certain embodiments of this aspect of the invention the processor is constructed and arranged to calculate the scattering coefficient at the wavelength in conjunction with creating the image data set.

Also, in certain embodiments, the processor is constructed and arranged to calculate the absorption coefficient at said wavelength in conjunction with creating the image data set.

In preferred embodiments the optical system is constructed to introduce and detect photons at two wavelengths selected to provide sensitivity to a property of the constituent.

In certain preferred embodiments, the source means of the optical system comprises an incandescent lamp, and preferably a set of miniature lamps directly contacting the subject.

In other preferred embodiments the source comprises a photo diode, and preferably a set of photo diodes directly contacting the subject.

According to another important aspect of the invention, an instrument is provided for functional imaging of brain activity of a subject comprising a brain imager, including an array of sources and detectors defining a multiplicity of source-detector pairs, constructed and arranged to image hemoglobin, deoxyhemoglobin or blood volume within the brain during administration of a respective stimulus to the subject, said brain imager including a processor receiving signals of the detected radiation from the detector, and constructed and arranged to create a defined spatial image of the functional activity of neural tissue by effectively producing a first data set representing, from a selected view, a spatial image of blood in the cortex while the subject is at rest, a second data set representing, from the same selected view, a spatial image of the blood in the cortex during stimulation, and a functional image data set that is related to the differences between the first and second data sets, over the sets.

Preferred embodiments of this aspect of the invention have one or more of the following features.

The device is in the form of a near infrared hemoglobinometer based on introducing and detecting photons that have migrated through tissue of the head, the device preferably having multiple source-detector pairs for engaging the skull, with the source being spaced from the detector for selected pairs between about 1.5 and 7 cm, preferably in certain instances the spacing being 2.5 cm or greater. The device has a multiplicity of light sources and detectors defining an array of source-detector pairs, and a control for energizing one source at a time enabling accumulation of single source-detector responses.

The light source or sources are incandescent lamps, LEDs, laser diodes or other lasers.

The instrument comprises an array of sources of near infrared or visible photons, an array of detectors positioned to receive photons from the sources in respective source-detector pairs following migration of the photons from the sources through the tissue, a system enabling numerous readings of migrated photons to be taken systematically at the detectors for different source-detector positions relative to the tissue, and a processor employing an imaging algorithm based on respectively different probabilities for a given source-detector position, for photons from the source passing through different regions of the volume of the scattering tissue that are located at different positions distributed laterally from a straight reference line between source and detector.

According to another important aspect of the invention, an instrument is provided for functional imaging of brain activity of a subject comprising an imager constructed and arranged to image hemoglobin, deoxyhemoglobin or blood volume, the imager comprising an array of sources of near infrared or visible photons, and array of detectors positioned to receive photons from the sources following migration of photons from the sources through the tissue, a system enabling numerous readings of migrated photons to be taken systematically for different source-detector positions relative to the tissue, and a processor employing data sets taken during rest and during stimulation, with an imaging algorithm that is based on respectively different probabilities for a given source-detector position, for photons from the source passing through different regions of the volume of the scattering tissue that are located at different positions distributed laterally from a straight reference line between source and detector.

The imaging algorithm is a back-projection algorithm, and the probabilities are implemented as respectively different weight factors employed in the algorithm for detected energy for different pixels of the image.

Instruments made according to the various main aspects of the invention may have one or more of the following features. The instrument is constructed to store at least one set of data for a given area of the brain while the subject is at rest and at least one set of data for the given area of the brain while the subject is stimulated, and to produce an output image representing the differences over the area of the respective sets of data.

The light sources produce relatively long light pulses and the instrument functions according to continuous wave spectroscopy, preferably the imaging instrument being constructed to take and employ readings at least at two different wavelengths.

An incandescent lamp is provided to produce the photons introduced at the sources, preferably an array of miniature incandescent lamps being arranged to be sequentially illuminated.

Each source is laterally displaced from its detector or detectors on the surface of a subject at a side by side spacing between about 1.5 and 7 cm to establish a banana-shaped probability gradient of migrating photons in the tissue that extends from source to detector.

The invention also features methods of producing an image from a volume of light-scattering tissue of a living subject comprising, providing and employing on the subject an imaging instrument according to any of the foregoing aspects. In certain preferred embodiments of the methods an optical contrast agent or a drug is introduced to the blood stream of the subject, and the instrument is employed to produce an image data set for the tissue while the contrast agent or drug is present in blood circulating in the tissue of the subject or is present in localized tissue.

These and other features and advantages of the invention will be understood from the drawings, the following description of preferred embodiments and the claims.

DESCRIPTION OF THE PREFERRED EMBODIMENTS

Figure 1:
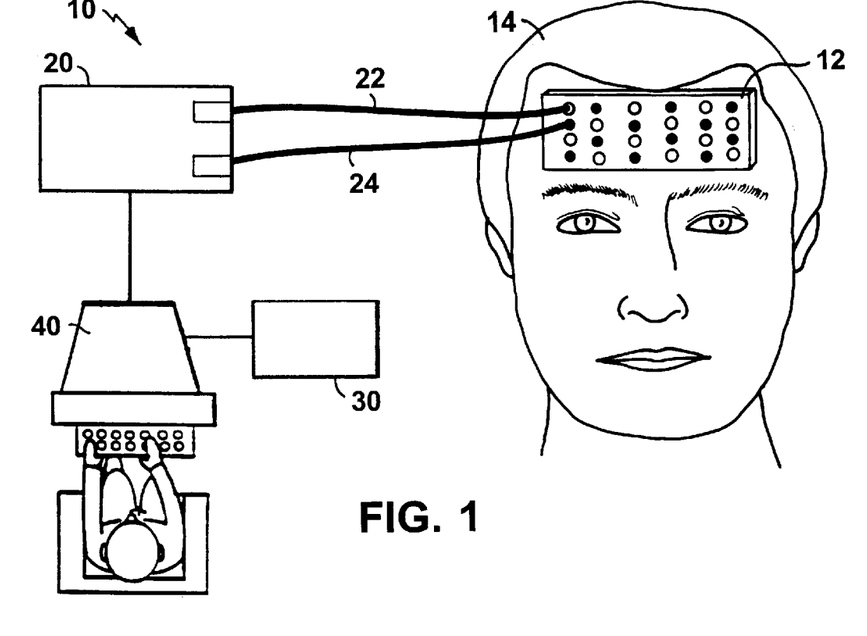
FIG. 1 depicts a block diagram of an optical tomography system for imaging functional activity of the brain.

An optical tomography system 10 for imaging functional activity of the brain includes a non-invasive, optical module 12, a spectrophotometer unit 20, a brain activity stimulation unit 30, and a computer and interface unit 40. Optical module 12, positioned on the forehead of the head 14, is operatively connected to spectrophotometer unit 20 by, for example, optical fibers 22 and 24. Computer and interface unit 40 automatically oversees and controls the operation of spectrophotometer unit 20, also stimulation unit 30.

Different embodiments of optical module 12 are disclosed in the PCT application PCT/US 96/00235, published as WO 96/20638 on Jul. 11, 1996 and in the PCT application PCT/US 96/11630, filed Jul. 12, 1996, both of which are incorporated by reference as if fully set forth herein. The optical module includes a plurality of optical input (irradiation) ports and optical detection ports located on a selected pattern. The ports are constructed to deliver in vivo electromagnetic radiation of a visible or infra-red wavelength into the brain at a selected irradiation location and collect the radiation that has migrated in the brain to a selected detection location. Furthermore, the construction of the input ports and detection ports also defines the size of the introduced and detected light beams, respectively. The optical module may also include a barrier, or a similar component, that absorbs superficial photons not propagating in the examined tissue.

Spectrophotometer unit 20 is a continuous wave spectrophotometer, as described in the WO 92/20273 publication published Nov. 26, 1996, now pending as U.S. patent application Ser. No. 08/150,084, which is incorporated by reference as if fully set forth herein. Alternatively, spectrophotometer unit 20 is a time resolved spectrophotometer, as described in the U.S. Pat. Nos. 5,119,815 and 5,386,827, or a phase modulation spectrophotometer, as described in the U.S. Pat. Nos. 4,972,331 and 5,187,672, and in the co-pending U.S. patent application Ser. No. 08/031,945 all of which are incorporated by reference as if fully set forth herein.

Stimulation unit 30 is constructed to stimulate a specific neural function of a subject. The stimulator, controlled by computer 40, emits mechanical, electrical, thermal, sound or light signals designed to stimulate the neural activity of interest. The neural activity is induced by sensory stimuli, such as visual, auditory, or olfactory stimuli, taste, tactile discrimination, pain and temperature stimuli, or proprioceptive stimuli.

Figure 2:
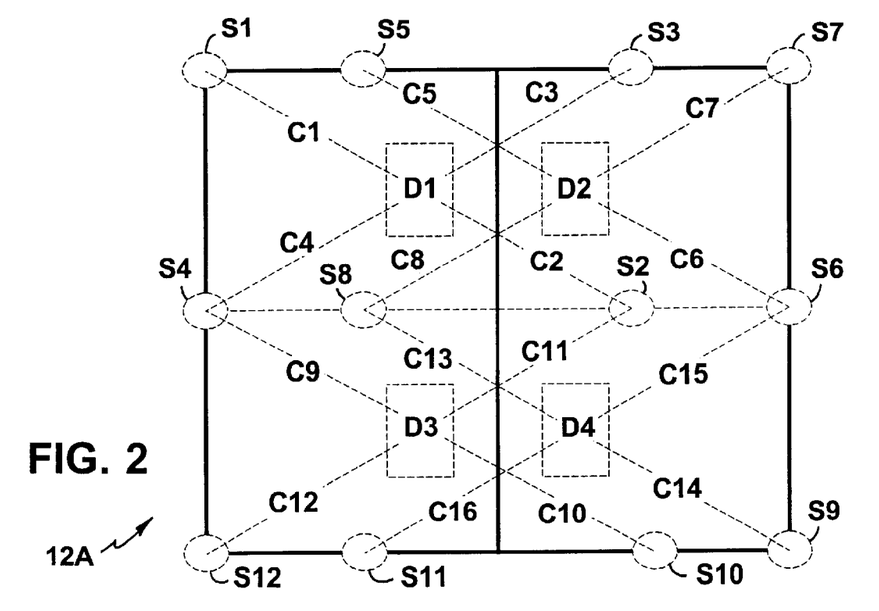
FIG. 2 depicts a diagram of an optical module employed in one preferred embodiment of the system of FIG. 1.

In a first preferred embodiment, a continuous wave spectrophotometer includes several sources and detectors attached to the optical module mounted on the head of the examined subject. Referring to FIG. 2, optical module 12a includes twelve light sources S1, S2, . . . , S12 and four light detectors D1, D2, D3, and D4 mounted on a plastic material. The light sources and the light detectors are located on a geometrical pattern that provides sixteen source-detector combinations (C1, C2, . . . , C16) having a selected source-detector separation. The separation was selected to be 2.5 cm, which produces about 1.25 cm average light penetration, to obtain a two dimensional image of the cortical surface. The light sources are 1 W tungsten light bulbs that are broad band light sources. The light detectors are silicon diodes, each equipped with an interference filter transmitting a 10 nm wide band centered at 760 nm and 850 nm. The 760 nm and 850 nm wavelengths are selected to detect oxyhemoglobin and deoxyhemoglobin in the examined cortex. (Depending on the physiological response, the wavelengths are in the visible to infrared range.)

Figure 2A:
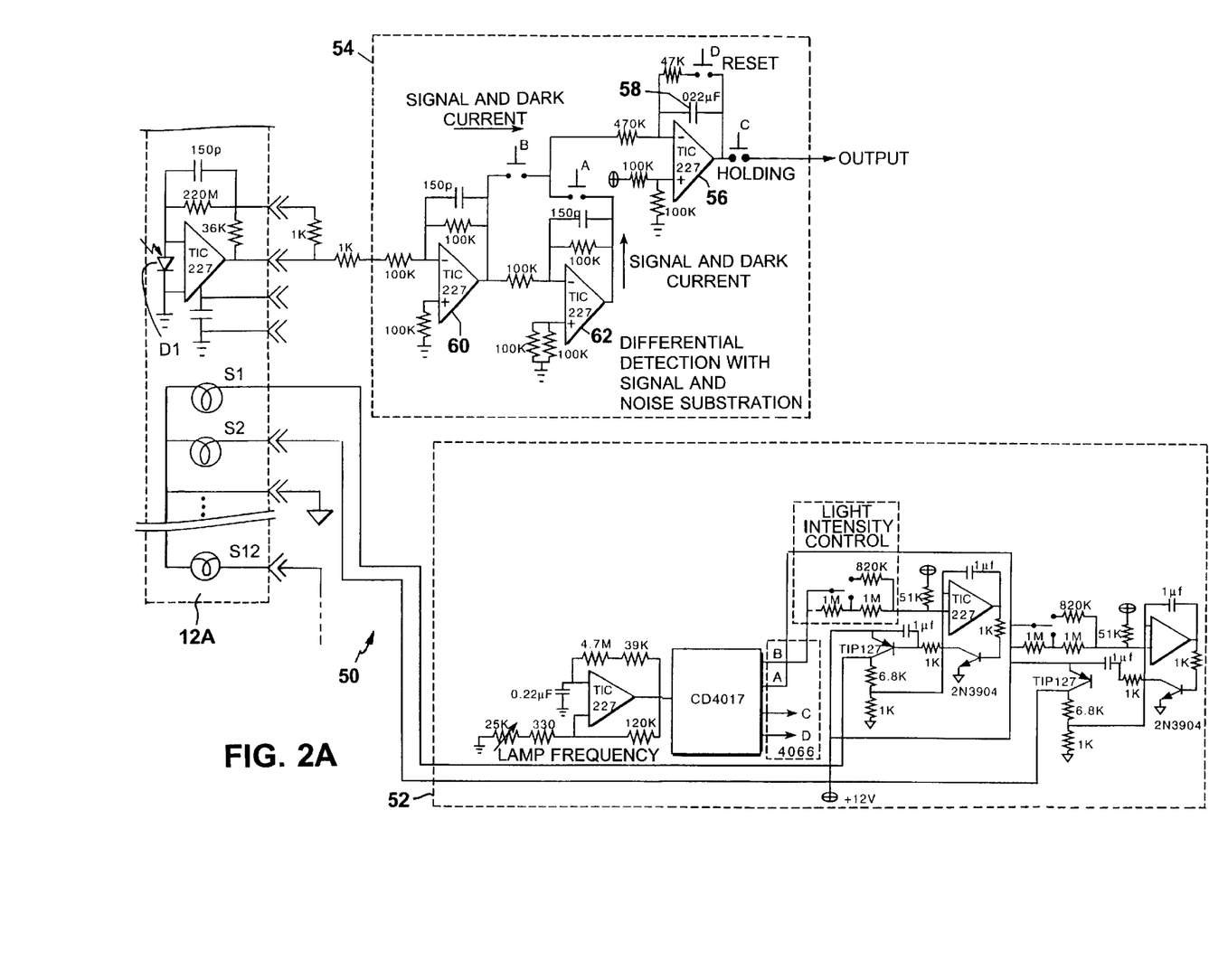
FIG. 2A depicts a schematic circuit diagram of a continuous wave spectrophotometer employed in one preferred embodiment of the system of FIG. 1.

Also referring to FIG. 2A, optical module 12A is connected to an analog circuit 50 that includes a source circuit 52 that controls sources S1, S2, . . . S12, and a detector circuit 54 that controls detectors D1, D2, D3 and D4. Each source is selectively turned on for a period of 500 msec. The emit light is introduced into the tissue from the corresponding input port and the photons migrate in the examined tissue to a detection port. The corresponding detector is triggered 200 msec. after the source and collects light for 200 msec.

Detector circuit 54 receives a detector signal from the diode detector. Detection circuit 54 enables correction for the dark current/noise that comprises background light, DC offset of the operational amplifiers, photodiode dark current, temperature effects on the outputs of individual components and variations due to changing environment.

The system performs data acquisition in four steps synchronized by its internal oscillator. The first step is performed by having the light sources off. The detector output is directed to an integrator 56 and integration capacitor 58 is charged to the dark level voltage. In the second step, the light source is turned on and after 200 msec. the preamplifier output that corresponds to the intensity of the detected light is directed to integrator 56 in a way to charge capacitor 58 with current of polarity opposite to the polarity of the charging current in the first step. This is achieved using an appropriate ON/OFF combination of switches A and B. The voltage of capacitor 58 is charging to a value which, after 200 msec., represents the total detected intensity minus the dark level noise signal. In the third step, both switches A and B are turned OFF to disconnect both the positive unity gain and the negative unity gain operational amplifiers (60 and 62). Then, the output of integrator 58 is moved via switch C to an analog-to-digital converter and the digital signal is stored in the memory of computer 60. In the fourth step, the switches A, B and C are open and switch D is closed in order to discharge capacitor 58 through a 47K resistor. At this point, the circuit of integrator 56 is reset to zero and ready for the first step of the detection cycle.

Alternatively, analog circuit 50 may be replaced by a computer with an analog-to-digital converter and appropriate software that controls the entire operation of optical module 12A. For instance a source code and be written in C language, to control the sources and the detectors of optical module 12A in a similar way as described above. The detected dark level noise signal is digitally subtracted from the detected intensity of the introduced light. A program can also be readliy written to transfers the raw data file, written in C, to another format for further use by the imaging algorithm.

This optical tomography system was used to image the activity of the visual cortex of a 54 year-old male subject while strictly observing the established safety protocol. Optical module 12A was placed on the occipital bone of the skull to observe the surface of the occipital cortex. A first data set was acquired for all sixteen C1 through C16 combinations with the subject having his eyes closed. A second data set was collected while the subject was watching a TV monitor. During a 40 second testing period, the subject was watching a circular object having a 5 cm diameter and a varying color. Next, the subject was asked to rest with closed eyes for two minutes. Then, a third data set was acquired for all sixteen source-detector combinations.

The collected data sets were processed using an imaging algorithm. The imaging algorithm calculated the blood volume in the examined cortex for each source-detector combination for the first, second and third data set. Then, the first data set of the blood volume was subtracted from the second data set of the blood volume to create a first differential image data set of volume difference between the testing period and the resting period. Next, the third data set of the blood volume was subtracted from the second data set of the blood volume to create a second differential image data set of volume difference between the testing period and the second resting period.

Figure 3A:
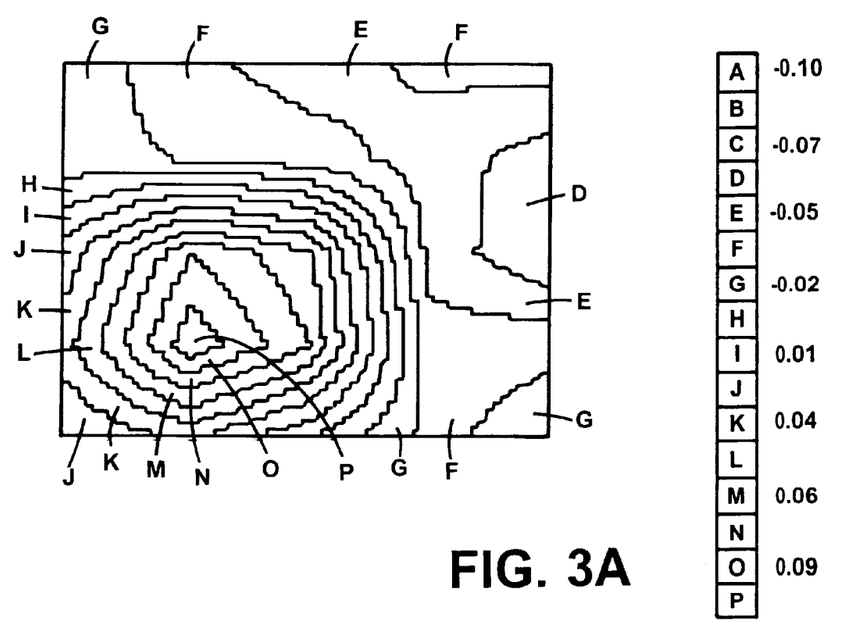
FIGS. 3A and 3B depict differential images of blood volumes detected on the visual cortex of a man watching a monitor screen and after a rest period of 2 minutes, respectively.
Figure 3B:
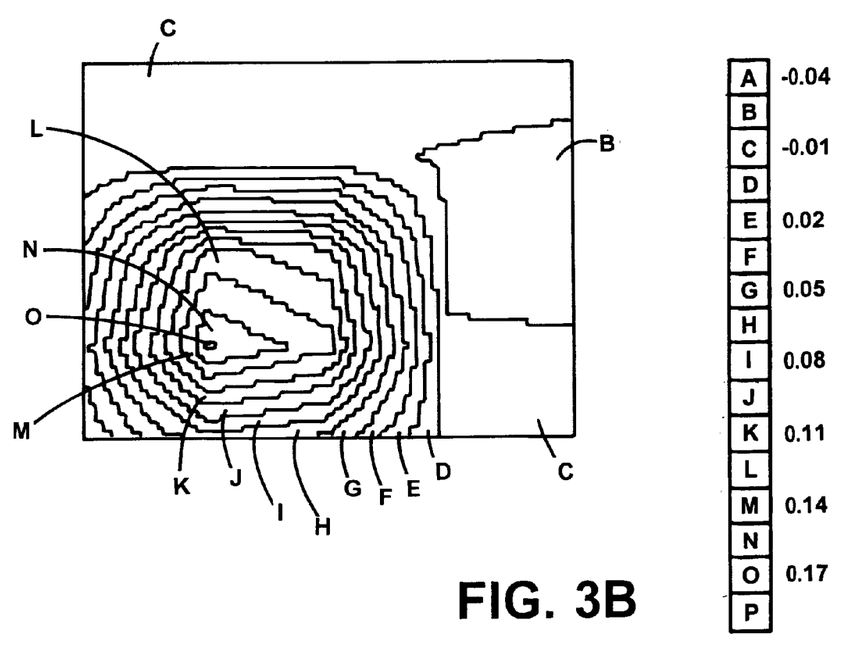

The imaging algorithm creates an image using the differential image data sets. Prior to creating the image, an interpolation algorithm is employed to expand the differential image data set, containing 16 (4×4) data points, to an imaging data set containing 32×32 image points. The image of the first volume difference between the testing period and the resting period is shown in FIG. 3A, and the image of the second volume difference between the testing period and the second resting period is shown in FIG. 3B. The images show an increased blood volume, which is accompanied with deoxygenation of hemoglobin in the imaged area.

Figure 4A:
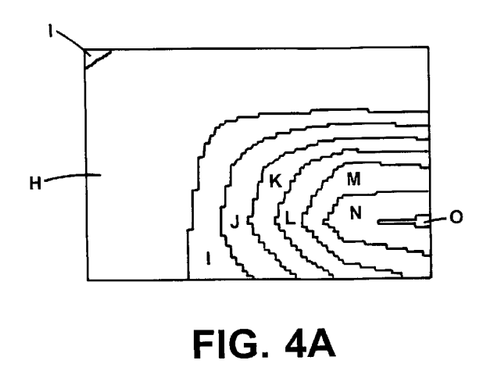
FIGS. 4A, 4B and 4C depict differential images of blood volumes of the motor cortex of a man tapping his fingers, after a rest period of 30 seconds, and restored rest volumes at 30–60 seconds, respectively.
Figure 4B:
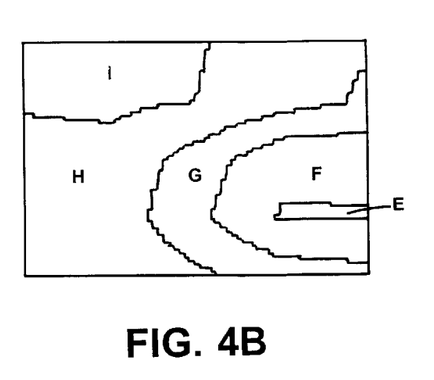
Figure 4C:
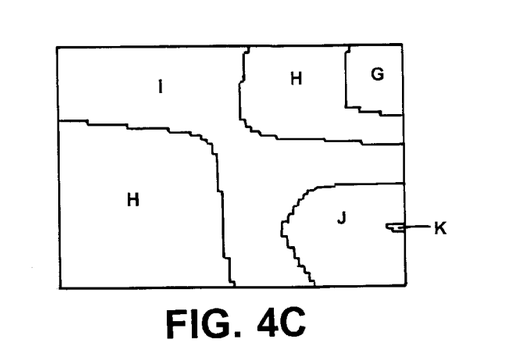

In another experiment, the optical tomography system was used to image the functional activity of the motor cortex of a subject. Optical module 12A was placed on the parietal bone of the skull to observe the surface of the parietal cortex. Similarly as above, a first data set was acquired for all sixteen C1 through C16 combinations with the subject having his fingers in rest. A second data set was collected while the subject was tapping as fast as possible for about 40 seconds, and a third data set was acquired after a rest period of 30 seconds. A fourth data set was acquired after a rest period of 30–60 seconds. FIGS. 4A, 4B and 4C depict differential images of blood volumes of the motor cortex of the subject man tapping his fingers, after a rest period of 30 seconds, and restored rest volumes at 30–60 seconds, respectively. The images show an increased blood volume, which is accompanied with desaturation of hemoglobin in the imaged area.

Figure 5A:
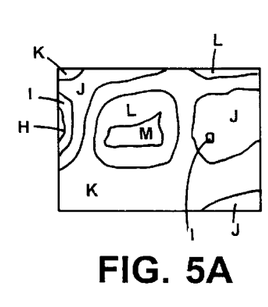
FIGS. 5A, 5B and 5C depict differential images of the hemoglobin oxygenation of the prefrontal cortex of a man translating words from English to French.
Figure 5B:
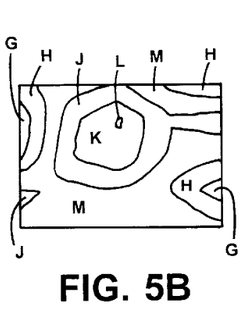
Figure 5C:
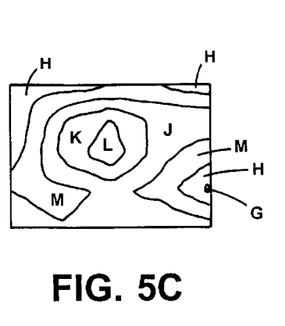
Figure 6A:
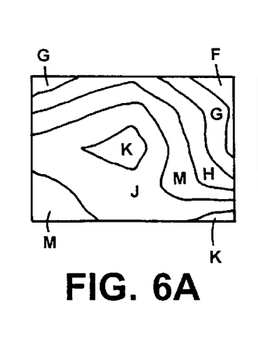
FIGS. 6A, 6B and 6C depict differential images of the blood volumes of the prefrontal cortex of a man translating words from English to French.
Figure 6B:
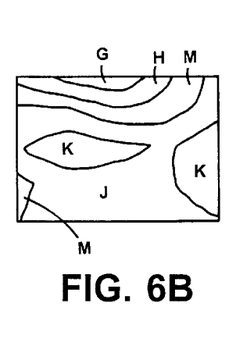
Figure 6C:
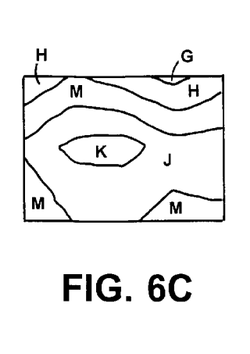

In another experiment, the optical tomography system was used to image the cognitive activity in the prefrontal cortex of a subject. A high school student was asked to translate words from English to French for 40 seconds with resting periods of 2 minutes. FIGS. 5A, 5B and 5C depict differential images of the hemoglobin oxygenation of the prefrontal cortex of a man translating words from English to French during three successive periods of 40 seconds. In an area of 0.5×2 cm of the prefrontal cortex, the images show repeated increased blood oxygenation due to the activation in a specific part of the cortex. However, the first image of the first stimulus produced the highest oxygenation increase. Similarly, FIGS. 6A, 6B and 6C depict differential images of the blood volumes in the same area of the prefrontal cortex during the translation from English to French.

In another important embodiment, a three dimensional image is created by producing slices of the above described two dimensional image at different depths of average photon penetration. The optical module includes a hairbrush optical coupler disclosed in the PCT application PCT/US 96/11630, filed Jul. 12, 1996, which is incorporated by reference as if fully set forth herein. The optical fibers are arranged in a geometrical pattern enabling different input detection port separations, for example, 1.5 cm, 2.0 cm, 2.5 cm, 3.0 cm, 3.5 cm, 4.0 cm, 4.5 cm, 5.0 cm, 5.5 cm, 6.0 cm, 6.5 cm, or 7.0 cm. For larger separations of the input and detection ports, the light source employs larger light intensities to obtain good signal to noise ratio. A two dimensional image is created for each average penetration depth, which is about ½ of the separation.

Figure 7:
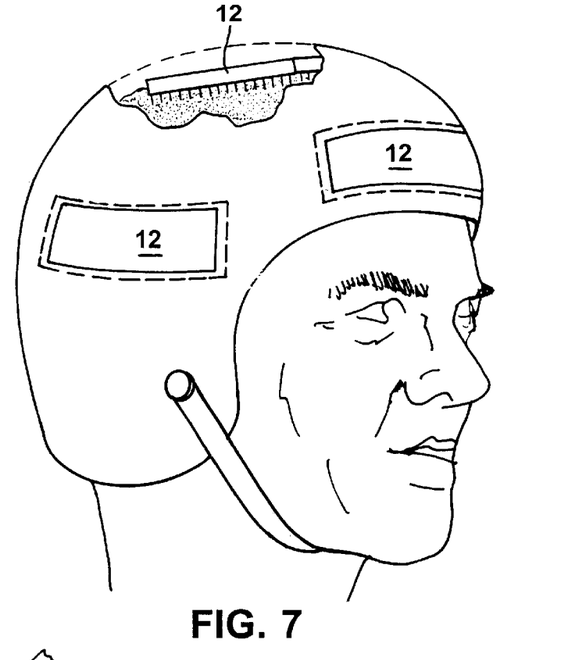
FIGS. 7, 7A and 7B depict a helmet constructed to attach the optical module to selected locations on the skull.
Figure 7A:
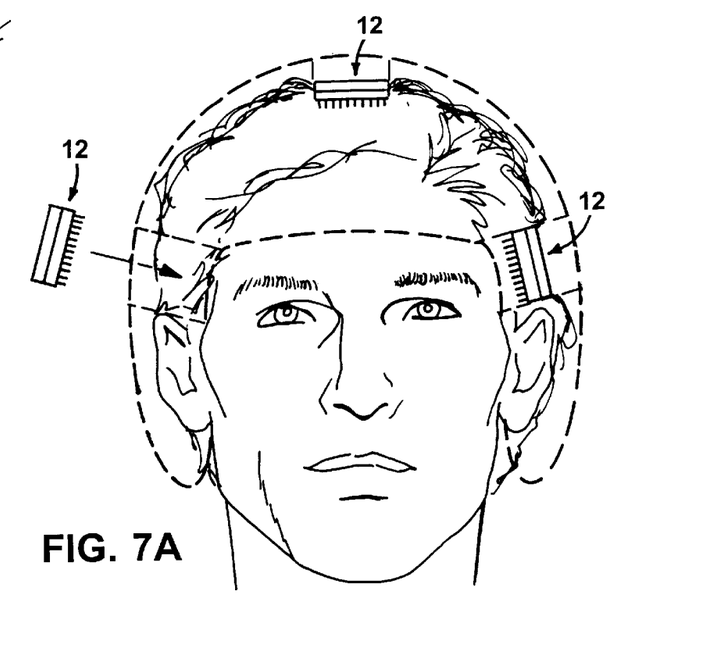
Figure 7B:
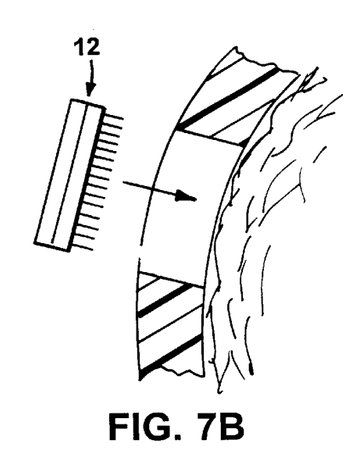

FIGS. 7, 7A and 7B depict a helmet constructed to attach optical module 12 to selected locations on the skull. This helmet enables reliable coupling of light to the examined tissue and eliminates different artifacts that may occur during acquisition of the image data due to the movement of the subject. This provides an important advantage over PET, CT, or FMRI all of which are subject to the unwanted artifacts.

The optical module is constructed to image a selected neural tissue, stimulated by the stimulator, by detecting the corresponding physiological response associated with the functional activity. The sources are constructed to emit and the detectors detect radiation of a wavelength sensitive to a physiological response of interest. The physiological response is a change in the blood volume, a change in the oxygenation state of a tissue pigment (endogenous pigment, such as hemoglobin, or exogenous pigment such as a contrast agent), a change in the scattering coefficient or refractive index of the tissue. Alternatively, the physiological response is generation or production of a metabolite that is detected by the introduced light either directly or indirectly (e.g., reaction with a exogenous agent introduced to the tissue).

The optical module is constructed to maintain a selected separation of the input and detection ports. In a reflection geometry, the photons of the introduced light migrate over a "banana" pattern with an average penetration depth about one half on the input-detection port separation. Thus, a neural region is targeted by the location and separation of the ports of optical module 12. The exterior locations of the ports depend on the targeted neural region. The locations of the neural regions have been extensively mapped in the prior art and are known to a person skilled in neuroanatomy and neurophysiology.

The computer uses a backprojection algorithm known in computed tomography (CT) modified for light diffusion and refraction and the banana like geometry employed by the optical imaging system. In the optical backprojection algorithm, the probabilistic concept of the "photon migration density" replaces the linear relationship of ballistically transmitted X-rays, for the beam representing pixels. The photon migration density denotes a probability that a photon introduced at the input port will occupy a specific pixel and reach the detection port. For different types of tissue, the phase modulation spectrophotometer provides the values of the scattering and absorption coefficients employed in the probability calculations. In the image reconstruction program, the probability is translated into a weight factor, when it is used to process backprojection. The backprojection averages out the values of information that each beam carries with the weighting in each pixel. The specific algorithms are embodied in the source code provided in Appendices E and F. Appendix E is a source code that incorporates a weighting algorithm for creating a photon density image used in the backprojection reconstruction algorithm disclosed in Appendix F.

A method for correcting blurring and refraction used in the backprojection algorithm was described by S. B. Colak, H. Schomberg, G. W. 't Hooft, M. B. van der Mark on Mar. 12, 1996, in "Optical BackProjection Tomography in Heterogeneous Diffusive Media" which is incorporated by reference as if fully set forth herein. The references cited in this publication provide further information about the optical backprojection tomography and are incorporated by reference as if fully set forth herein.

The optical tomography system can also image numerous other centers of the neural activity. For example, optical module 12 is attached to the temporal bone of the skull to examine the surface of the temporal lobe. Then, the stimulator stimulates the auditory function while the optical tomography system images neurofunctional activity of the auditory area of the temporal lobe. The optical system may also image the auditory association cortex of Wernicke in the temporal lobe before and after stimulation by the stimulator.

In other neurofunctional examination, optical module 12 is attached to the frontal bone of the skull to examine the frontal lobe. Then, the stimulator stimulates the motor speech function while the optical tomography system images neurofunctional activity of the motor speech area of Broca before and during stimulation. Additionally, optical module 12 may attached to the right parietal bone to examine the neurofunctional activity of the general sensory area before and during stimulation of pain, hot or cold sensation, or vibrational sensation on the left extremities, and vice versa.

Alternatively, the stimulation unit is constructed to induce physiologic and pathologic reflexes in the cerebral or spinal tissue. The stimulation unit stimulates pupillary reflexes, corneal reflexes, oculocephalic reflexes, oculovestibular reflexes, deep tendon reflexes, abdominal reflex, cremasteric reflexes, postural reflexes, gag reflex, infantile reflexes (such as blinking reflex, cochleopalpebral reflex, palmar grasp reflex, digital response reflex, rooting reflex, Galant's reflex, tonic neck reflex, Perez reflex, startle reflex).

The stimulator stimulates a selected region of the nervous system. The corresponding neurologic impulses, transmitted by the neurons, are detected and imaged at different points of their paths, for example, in the nerves, in the spinal cord, in the thalamus, or in the cerebral cortex. For example, when the stimulator causes a cold or hot stimulation on the little finger of the left hand, this thermal stimulation produces impulses that travel in the right lateral spinothalamic tract of the cervical spinal cord, to the thalamic sensory nuclei and end in the right postcentral gyrus of the parietal lobe.

What is claimed is:

1. An optical system for in vivo, non-invasive imaging of biological tissue comprising:

an optical module including an array of input and detection ports located in a selected geometrical pattern to provide a multiplicity of arrayed source-detector pairs constructed and arranged to be engaged directly with a subject;

a spectrophotometer including a light source constructed to introduce electromagnetic radiation of a visible or infra-red wavelength into the examined tissue successively at said input ports, said wavelength being sensitive to a constituent of the imaged tissue;

a light detector constructed to detect radiation of said wavelength that has migrated in the tissue from respective input ports to associated detection ports; and a processor receiving signals of said detected radiation from said detector, and constructed and arranged to create a defined spatial image of the tissue by effectively producing from signals from the multiplicity of arrayed source-detector pairs, a succession of data sets representing, from a selected view, a succession of spatial images of the tissue, and an image data set related to differences between data of said successive data sets.

2. The optical system of claim 1 wherein said optical module is constructed to prevent migration of superficial photons migrating on a tissue surface between said input and detection ports.

3. The optical system of claim 1 wherein said optical module is constructed to be positioned on the exterior surface of the head and also constructed to prevent migration of superficial photons migrating on a tissue surface between said input and detection ports.

4. The optical system of claim 1 wherein said optical module is constructed to include one said light source associated with one said input port and include one said light detector associated with one said detection ports for the respective source-detector pairs.

5. The optical system of claim 1 wherein said optical module is constructed to maintain a selected distance between said input and detection ports for the respective source-detector pairs during the production of said first and second data sets, said distance being selected according to the tissue depth desired to be imaged.

6. The optical system of claim 5 wherein said processor is constructed to produce 2D data sets for said tissue depth.

7. The optical system of claim 1 wherein said processor is constructed to produce 3D data sets from which said image data set, related to said differences, is produced.

8. The optical system of claim 7 wherein said processor is programmed to produce said image data set by implementing an optical tomography algorithm.

9. The optical system of claim 8 wherein said processor employs in said optical tomography algorithm factors related to determined probability distribution of photons attributable to the scattering character of the tissue being imaged.

10. The optical system of claim 7 wherein said processor is programmed to generate said image set is related to at least one of the group consisting of blood volume, hemoglobin oxygenation, hemoglobin deoxygenation, photon absorption coefficient, photon scattering coefficient, and refractive index.

11. The optical system of claim 1 wherein said processor is programmed to produce said image data set by implementing an optical tomography algorithm.

12. The optical system of claim 1 wherein said processor is programmed to generate said image data set from a tissue part of the head.

13. The optical system of claim 1 wherein said processor is programmed to generate said image set related to at least one of the group consisting of: blood volume, hemoglobin oxygenation, hemoglobin deoxygenation, photon absorption coefficient, photon scattering coefficient, and refractive index.

14. The optical system of claim 1 in which each source is laterally displaced from said respective detector on the surface to be engaged with the subject at a side by side spacing between about 1.5 and 7 cm to establish a banana-shaped probability distribution of migrating photons in the tissue that extends between the respective input and detection ports.

15. A method of in vivo, non-invasive imaging of tissue change comprising:

providing an array of input locations and detection locations arranged over a selected geometrical pattern to provide a multiplicity of photon migration paths in the tissue, introducing electromagnetic radiation of a visible or infra-red wavelength into the tissue selectively at said input locations, said wavelength being sensitive to a constituent of the tissue;

detecting, at said detection locations, radiation of said selected wavelength that has migrated in the tissue from at least one input location; and creating a defined spatial image of the tissue based on signals from said multiplicity of said photon migration paths, a succession of data sets representing, from a selected view the tissue of interest, and an image data set related to differences between data of said successive data sets of the tissue of interest.

16. The imaging method of claim 15 including detecting radiation for a selected input and detection separation to produce 2D data sets.

17. The imaging method of claim 15 including detecting radiation for different input and detection separation to produce 3D data sets.

18. The imaging method of claim 15 further including calculating said image related to at least one of the group consisting of: blood volume, hemoglobin oxygenation, hemoglobin deoxygenation.

19. The imaging method of claim 15 further employing a second wavelength.

20. The imaging method of claim 15 further including introducing an optical contrast agent to the blood stream of the subject, and producing said image data sets for the tissue while the contrast agent is present in the blood circulating in the tissue of the subject.

21. The imaging method of claim 15 further including introducing a drug to the blood stream of the subject, and producing said image data sets for the tissue while the drug is present in the blood circulating in the tissue of the subject.

* * * * *